United States Patent [19]

Roman

[11] 4,132,717
[45] Jan. 2, 1979

[54] ENOL LACTONE INTERMEDIATE FOR THE PREPARATION OF (1R,CIS)-CARONALDEHYDIC ACID

[75] Inventor: Steven A. Roman, Oakdale, Calif.

[73] Assignee: Shell Oil Company, Houston, Tex.

[21] Appl. No.: 823,233

[22] Filed: Aug. 9, 1977

[51] Int. Cl.$^2$ .......................................... C07D 311/94
[52] U.S. Cl. ...................... 260/343.21; 260/343.3 R; 260/546; 562/506
[58] Field of Search ................................. 260/343.21

[56] References Cited

U.S. PATENT DOCUMENTS

| | | | |
|---|---|---|---|
| 3,565,915 | 2/1971 | Matsui | 260/343.21 |
| 3,723,469 | 3/1973 | Martel | 260/343.3 |
| 3,922,286 | 11/1975 | Yoshioka et al. | 260/343.21 |
| 3,989,654 | 11/1976 | Honda et al. | 260/343.21 |

OTHER PUBLICATIONS

Hirai et al., Chem. Abstracts, 84, 105801z.

*Primary Examiner*—Natalie Trousof
*Assistant Examiner*—Jane T. Fan

[57] ABSTRACT

(1R,cis)-caronaldehydic acid is prepared from (+)-$\Delta^3$-carene by a multistep process in which the (+)-$\Delta^3$-carene derivative, (1R,cis)-2,2-dimethyl-3-(2-oxopropyl)cyclopropane-1-carboxylic acid, is cyclodehydrated, the resulting novel intermediate enol lactone is treated with ozone, the resulting ozonide is subjected to reductive cleavage to afford the mixed anhydride of the open form of (1R,cis)caronaldehydic acid and this mixed anhydride is hydrolyzed to the desired product. The intermediate enol lactone is a new compound.

1 Claim, No Drawings

ENOL LACTONE INTERMEDIATE FOR THE PREPARATION OF (1R,CIS)-CARONALDEHYDIC ACID

BACKGROUND OF THE INVENTION

1. Field of the Invention

The present invention is directed to a process for the preparation of (1R,cis)-caronaldehydic acid and to certain novel intermediates in the process.

2. Description of the Prior Art

U.S. Pat. No. 3,732,469 describes (1R,cis)-caronaldehydic acid (the internal hemiacylal of (1R,cis)-3,3-dimethyl-2-formyl-cyclopropane-1-carboxylic acid) as an intermediate for the preparation of certain 2,2-dimethyl-3-substituted-vinyl-cyclopropane-1-carboxylic acids, the starting material for the preparation of (1R,cis)-caronaldehydic acid being (1R, trans)-chrysanthemic acid.

The present process affords a method for preparing (1R,cis)-caronaldehydic acid ultimately from the very inexpensive, abundant and readily available natural terpene, (+)-$\Delta^3$-carene.

SUMMARY OF THE INVENTION

The process of the invention comprises the preparation of (1R,cis)-caronaldehydic acid by cyclodehydrating (1R,cis)-2,2-dimethyl-3-(2-oxopropyl) cyclopropane-1-carboxylic acid, treating the resulting enol lactone with ozone, effecting reductive cleavage of the ozonide to afford the mixed anydride of the open form of (1R,cis)-caronaldehydic acid and hydrolyzing the anhydride.

More specifically, the invention provides an efficient process for the preparation of (1R,cis)-caronaldehydic acid represented by formula I

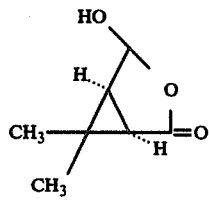

in which one subjects (1R,cis)-2,2-dimethyl-3-(2-oxopropyl)-cyclopropane-1-carboxylic acid represented by formula II

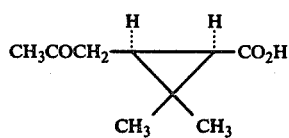

to cyclodehydration to produce an enol lactone of formula III

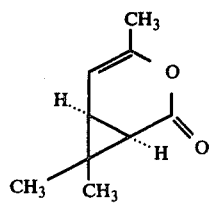

and subjects this compound to ozonization to yield the mixed anhydride of (1R,cis)-caronaldehydic acid represented by formula IV

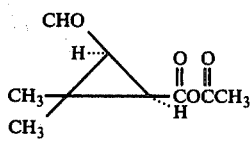

and hydrolyzing this anhydride to yield (1R,cis)-caronaldehydic acid.

The cyclodehydration is conducted under acidic conditions. For example, the (1R,cis)-2,2-dimethyl-3-(2-oxopropyl) cyclopropane-1-carboxylic acid starting material can be treated at 10° to 80° C. with a catalytic amount of p-toluenesulfonic acid and an organic acid anhydride, such as acetic anhydride, in an inert solvent, for example an aromatic hydrocarbon such as benzene, toluene or the like.

The ozonization is conducted using various procedures known in the art, for example, using ozone gas optionally diluted with oxygen gas, nitrogen gas or air at a low temperature of −80° to 30° C., preferably below 0° C. Conveniently the enol lactone is dissolved in a solvent which is inert to the ozonization reaction. Suitable solvents include aromatic hydrocarbons such as benzene and toluene, halogenated hydrocarbons, such as methylene dichloride, chloroform, and the like, lower aliphatic carboxylic acids and esters thereof such as glacial acetic acid, ethyl acetate, and the like, aliphatic hydrocarbons, such as n-hexane and the like, and lower alkanols such as methanol.

The resulting ozonide is subjected to the next reaction step with or without separation from the reaction mixture. A solution of the ozonide in a suitable solvent, e.g, an ether or aromatic hydrocarbon such as diethyl ether, benzene, toluene or the like, is treated to effect reductive cleavage, for example by treatment with zinc dust and acetic acid at a temperature of about 10–30° C. When such a reaction is conducted in the absence of added water it affords the mixed anhydride (IV) of (1R,cis)-caronaldehydic acid. In such case, the addition at about room temperature of an aqueous base, such as alkali or alkaline earth metal hydroxide, preferably sodium hydroxide or potassium hydroxide or the like, preferably in combination with a solvent, such as acetone, yields the desired (1R,cis)-caronaldehydic acid. However, if the zinc-acetic acid treatment is conducted in the presence of water, e.g., using ether-acetic acid-water solvent of ratio 40:9:1, then the (1R,cis)-caronaldehydic acid is produced directly. The amount of water present is at least the stoichiometric amount required for the reaction to proceed. The amount of water should also be sufficient to maintain the homogenity of the solvent system used. In either case, the acid can be recovered and purified by known techniques such as extraction, filtration and the like.

An advantage of the present process is that (1R,cis)-2,2-dimethyl-3-(2-oxopropyl) cyclopropane-1-carboxylic acid can be prepared starting from (+)-$\Delta^3$- carene as disclosed in Agr. Biol. Chem., 29, 784 (1965) in which (+)-$\Delta^3$-carene was subjected to ozonolysis, the resulting 2,2-dimethyl-3-cis-(2-oxopropyl) cyclopropyl-1-acetaldehyde was treated with sodium acetate in acetic anhydride and fractionally separated under reduced pressure to give the corresponding aldehyde-enol acetate, ozonolysis of this intermediate followed by reduction with zinc dust in acetic acid gave 2,2-dimethyl-3-cis-(2-oxopropyl) cyclopropane-1-aldehyde as a product recovered from the neutral portion of the reaction medium and this aldehyde was oxidized with aqueous alkaline potassium permangate or gaseous oxygen to afford (1R,cis)-2,2-dimethyl-3-(2-oxopropyl) cyclopropane-1-carboxylic acid. If an optically active, i.e., (+) or (−)-Δ$^3$-carene is employed in the disclosed process, then the corresponding optically active acid is obtained. (+)-Δ$^3$-Carene is an inexpensive, readily available, naturally occurring terpene found in numerous varieties of pine trees and can be readily purified by fractional distillation.

As has been previously mentioned the product (1R,cis)-caronaldehydic acid is useful to prepare certain 2,2-dimethyl-3-substituted-vinyl-cyclopropane-1-carboxylic acids, which themselves are intermediates in the preparation of synthetic pyrethroids having useful insecticidal properties.

EXAMPLES

The process of the invention is demonstrated in the following examples which are for the purpose of illustration only and should not be regarded as limiting the invention in any way. In the examples, the identities of compounds, intermediates and final product, were confirmed by elemental analysis, and infrared and nuclear magnetic spectral analyses as necessary.

EXAMPLE I (1R,cis)-4,7,7-Trimethyl-3-oxabicyclo[4.1.0]hept-4-en-2-one (Compound of Formula III)

A solution of 29 g (0.17 mol) of (1R,cis)-2,2-dimethyl-3-(2-oxopropyl) cyclopropane-1-carboxylic acid and 3 g (0.016 mol) of p-toluenesulfonic acid monohydrate in 93 ml of acetic anhydride and 150 ml of benzene was stirred for 30 minutes at 10°–20° C. The slightly darkened mixture was diluted with ether and washed with ice cold saturated sodium bicarbonate solution until the washings were basic. The organic phase was dried over anhydrous magnesium sulfate and decolorized with charcoal. The solvent was evaporated in vacuo to give 24 g (93%) of the product as a tan solid. Recrystallization from pentane gave a white solid (III) m.p. 44–45.5° C., $[\alpha]_D{}^{25}$-85.6° (c,2.0,CHCl$_3$).

EXAMPLE II (1R,cis)-Caronaldehydic acid

A stream of ozone in air was bubbled into a solution of 18.2 g (0.12 mol) of the product of Example I in 100 ml of methylene chloride at −80° C. until a faint blue color persisted. The solution was purged with air to remove excess ozone and the solvent was evaporated under reduced pressure below 25° C. The residue was dissolved and stirred in 480 ml of ether-acetic acid-water (40:9:1) and treated portionwise with 43.2 g of zinc dust over 1.5 hours while maintaining the temperature at about 20° C. After stirring for 2 hours at ambient temperature, the mixture was filtered to remove zinc salts and the filtrate was evaporated in vacuo. The residue, in methylene chloride, was dried over anhydrous magnesium sulfate and the solvent was evaporated to provide, on trituration with pentane-ether (4:1), 11.8 g of product, m.p. 112–113° C. The residue from the filtrate provided an additional 0.8 g for a total yield of 74%. Recrystallization from ether-pentane gave a white solid, m.p. 116–117.5° C., $[\alpha]_D{}^{28}$-101.5° (c,1.1;EtOH).

EXAMPLE III (1R,cis)-Caronaldehydic acid

An ozonide was prepared as in Example II. However, zinc decomposition of the ozonide was conducted in the absence of added water to provide a crude mixture of the acetic acid mixed anhydride (of formula IV) of the open form of (1R,cis)-caronaldehydic acid in 82% yield, as indicated by the presence of strong anhydride bands in the infrared spectrum. A mixture of 3.8 g of the crude mixed anhydride, 20 g of 10% aqueous sodium hydroxide and 20 ml of acetone was stirred for 1 hour at room temperature. The resulting solution was washed with ether and the aqueous phase was acidified with dilute hydrochloric acid. Extraction with chloroform provided 0.8 g of product; m.p. 115.5–116° C.

I claim:

1. A compound of the formula

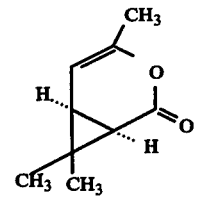

in the 1R,cis form.

* * * * *